US009636104B2

(12) United States Patent
Mohajer-Shojaee

(10) Patent No.: US 9,636,104 B2
(45) Date of Patent: May 2, 2017

(54) LAPAROSCOPIC CANNULA WITH SUTURING PASSAGE CUTOFF

(71) Applicant: Reza Mohajer-Shojaee, Encino, CA (US)

(72) Inventor: Reza Mohajer-Shojaee, Encino, CA (US)

( * ) Notice: Subject to any disclaimer, the term of this patent is extended or adjusted under 35 U.S.C. 154(b) by 26 days.

(21) Appl. No.: 14/710,669

(22) Filed: May 13, 2015

(65) Prior Publication Data

US 2015/0238184 A1 Aug. 27, 2015

Related U.S. Application Data

(63) Continuation-in-part of application No. 13/984,240, filed as application No. PCT/US2012/025373 on Feb. 6, 2012, now Pat. No. 9,033,872.

(60) Provisional application No. 61/443,286, filed on Feb. 16, 2011, provisional application No. 62/090,953, filed on Dec. 12, 2014.

(51) Int. Cl.
A61B 17/04 (2006.01)
A61B 17/00 (2006.01)
A61B 17/34 (2006.01)
A61B 17/02 (2006.01)
(Continued)

(52) U.S. Cl.
CPC ...... *A61B 17/0469* (2013.01); *A61B 17/0057* (2013.01); *A61B 17/0218* (2013.01); *A61B 17/0482* (2013.01); *A61B 17/0485* (2013.01); *A61B 17/06066* (2013.01); *A61B 17/3421* (2013.01); *A61B 17/3423* (2013.01); *A61B 17/3498* (2013.01); *A61B 17/3474* (2013.01); *A61B 2017/00637* (2013.01); *A61B 2017/00663* (2013.01); *A61B 2017/0472* (2013.01); *A61B 2017/347* (2013.01);
(Continued)

(58) Field of Classification Search
CPC . A61B 17/3421; A61B 17/3423; A61B 17/02; A61B 17/0218; A61B 17/0482
USPC ............ 600/201–210, 215, 235, 213; 604/158–161, 167.01–167.06
See application file for complete search history.

(56) References Cited

U.S. PATENT DOCUMENTS 5,300,035 A * 4/1994 Clement ........... A61M 39/0613
604/167.01
5,507,758 A 4/1996 Thomason et al.
(Continued)

FOREIGN PATENT DOCUMENTS

EP 1219253 A1 7/2002

OTHER PUBLICATIONS

International Search Report—International Application No. PCT/US2012/025373.

*Primary Examiner* — Matthew Lawson
*Assistant Examiner* — Amy Sipp
(74) *Attorney, Agent, or Firm* — Dinsmore & Shohl LLP

(57) ABSTRACT

A cannula for use in laparoscopic surgery has a central passage which may accept a trocar to create a laparoscopic incision in a body wall to an inner body cavity. A tubular section of the cannula is then pressed into the incision to form a port. The tubular section has passages through its walls for suturing needles and a source for insufflating gas. A tubular sleeve is slidably supported on the outer side of the tubular cannula for movement between a raised position clear of the needle passage exit ports and a lowered position blocking the exit ports to prevent insufflation gases from passing into the body wall.

7 Claims, 9 Drawing Sheets

(51) Int. Cl.
*A61B 17/06* (2006.01)
*A61M 13/00* (2006.01)
(52) U.S. Cl.
CPC ................ *A61B 2017/3445* (2013.01); *A61B 2017/3449* (2013.01); *A61M 13/003* (2013.01)

(56) References Cited

U.S. PATENT DOCUMENTS

| | | | |
|---|---|---|---|
| 5,716,369 A * | 2/1998 | Riza | A61B 17/0469 606/139 |
| 5,993,471 A * | 11/1999 | Riza | A61B 17/3498 606/185 |
| 8,808,248 B2 | 8/2014 | Schultz | |
| 2005/0096507 A1 * | 5/2005 | Prosek | A61B 17/34 600/204 |
| 2008/0097485 A1 | 4/2008 | Shpaichler et al. | |
| 2008/0255519 A1 | 10/2008 | Piskun et al. | |
| 2009/0012447 A1 | 1/2009 | Huitt et al. | |
| 2010/0002958 A1 | 1/2010 | Wu | |
| 2010/0240959 A1 * | 9/2010 | Donahue | A61B 17/3421 600/204 |
| 2010/0256567 A1 | 10/2010 | Smith | |
| 2011/0218568 A1 * | 9/2011 | Voss | A61B 17/04 606/232 |
| 2012/0010471 A1 * | 1/2012 | Mire | A61M 29/00 600/210 |
| 2012/0035623 A1 | 2/2012 | Bagaoisan et al. | |

* cited by examiner

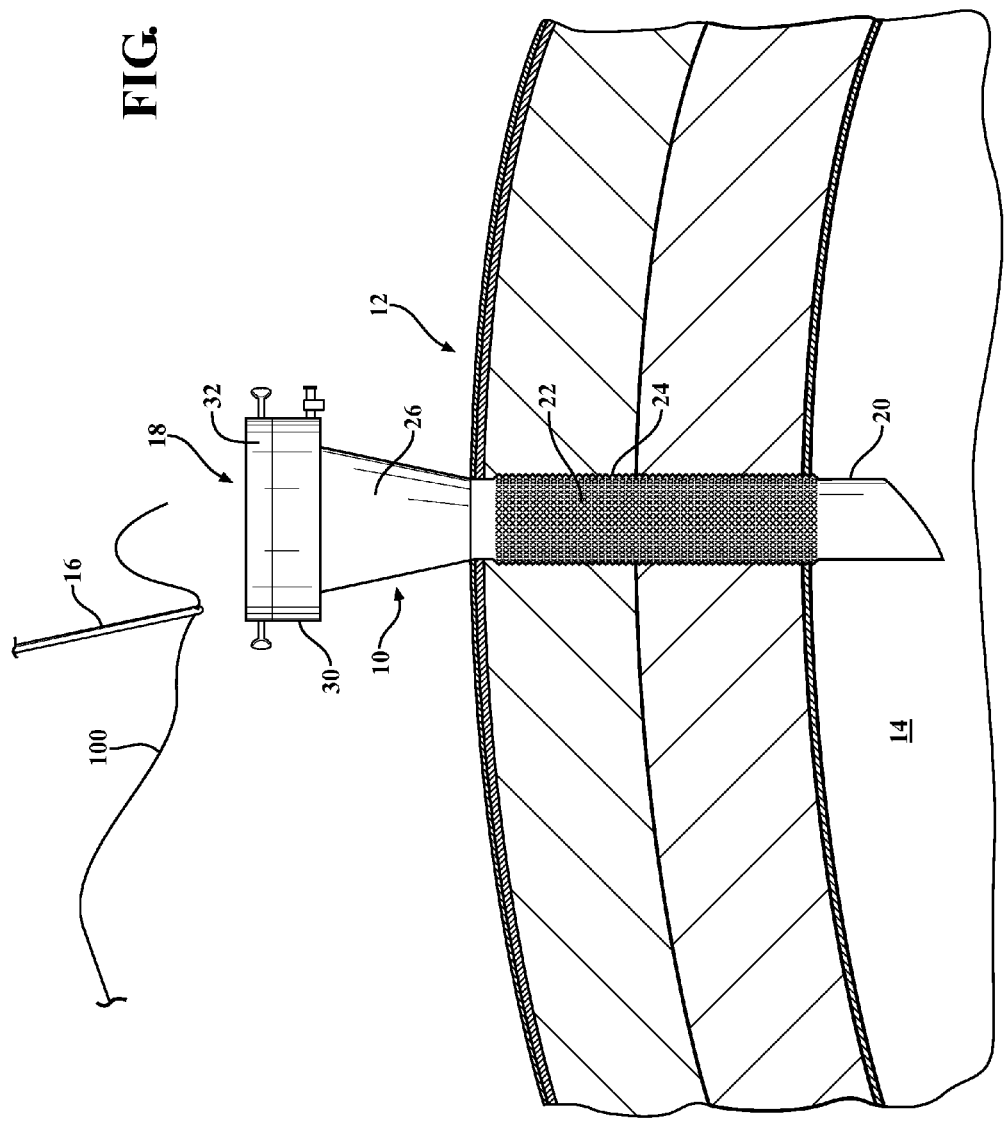

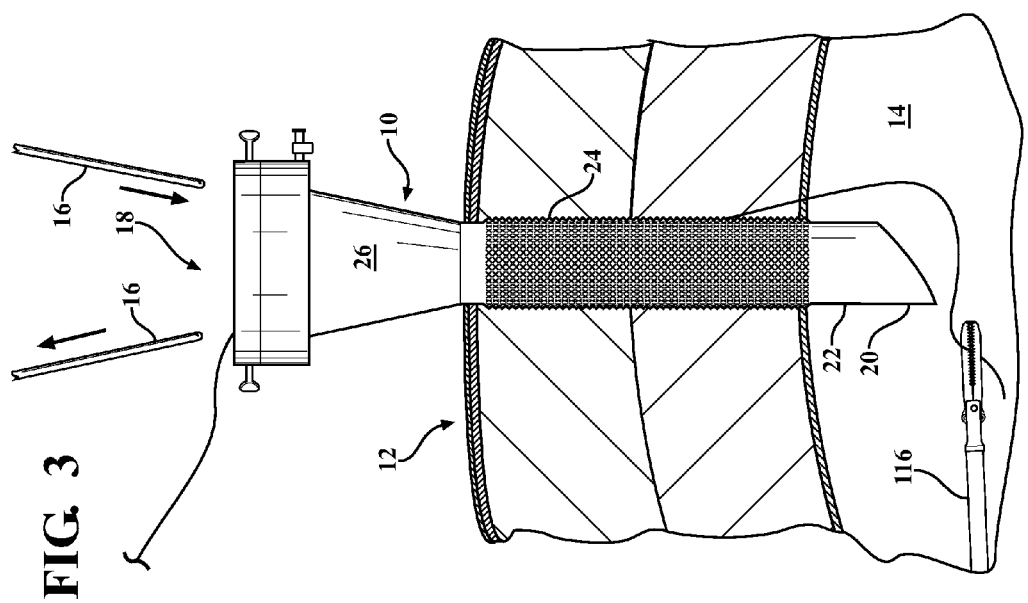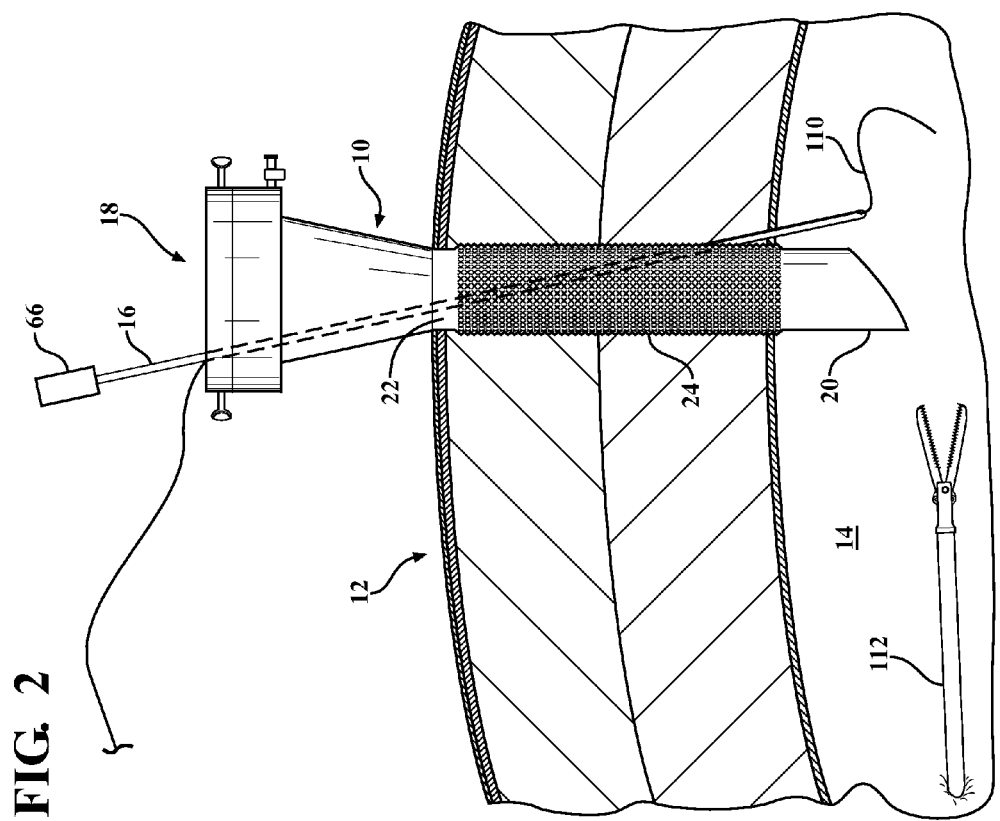

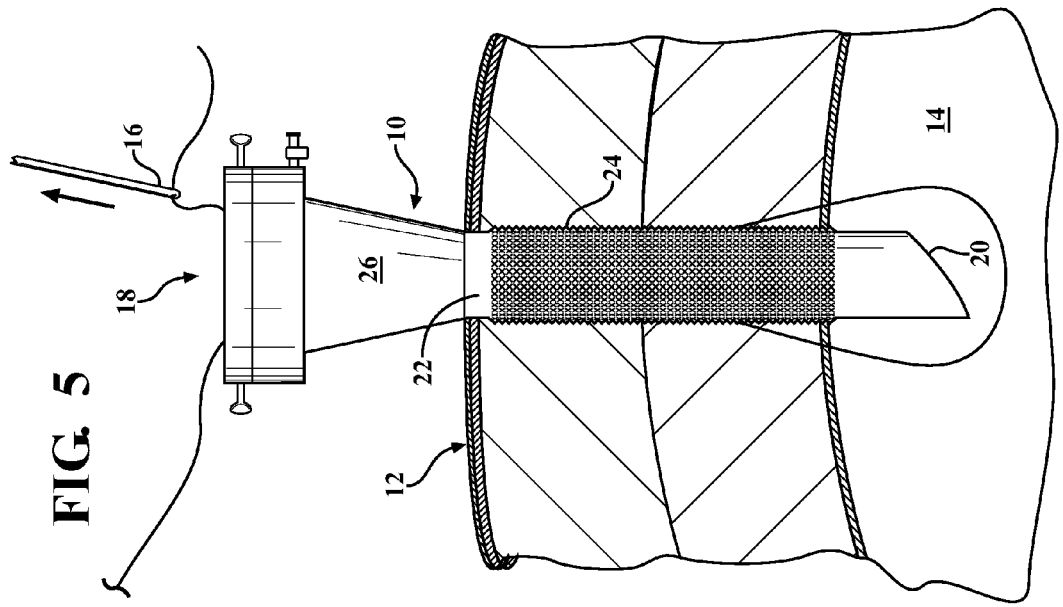
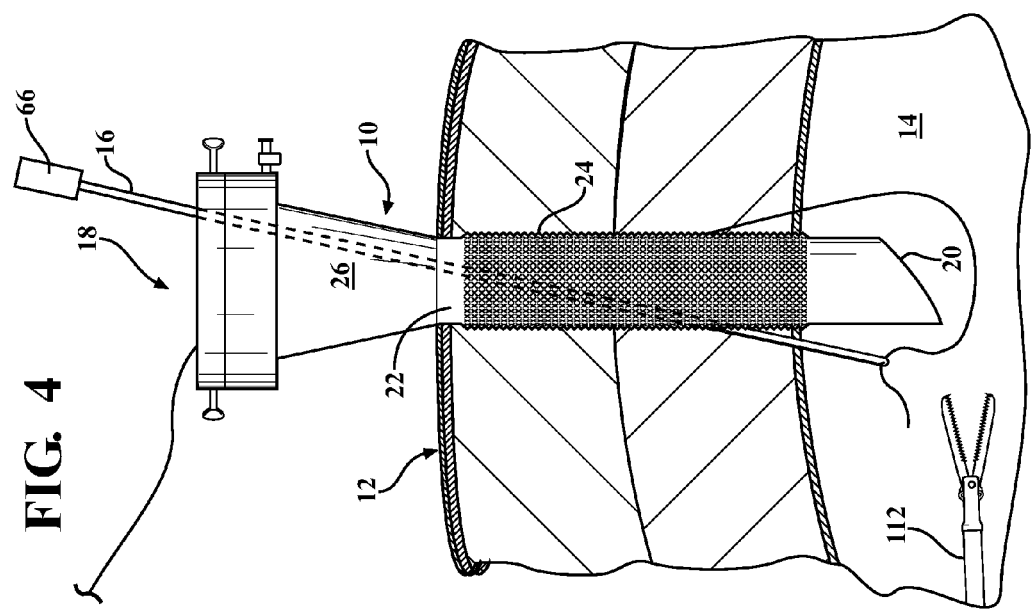

LAPAROSCOPIC CANNULA WITH SUTURING PASSAGE CUTOFF

CROSS-REFERENCE TO RELATED APPLICATIONS

This application is a continuation-in-part of U.S. patent application Ser. No. 13/984,240 filed Feb. 19, 2014, which is the U.S. national stage of PCT/US2012/025373 filed Feb. 16, 2012, which claims priority of U.S. Provisional Patent Application No. 61/443,286 filed Feb. 16, 2011, and claims the benefit of priority of U.S. Provisional Patent Application No. 62/090,953 filed Dec. 12, 2014, the contents of which are incorporated herein by reference.

FIELD OF THE INVENTION

This invention relates to cannulas and accessories for use in laparoscopic surgery and more particularly to a cannula enabling suturing of a laparoscopic incision.

BACKGROUND OF THE INVENTION

In the performance of a laparoscopic operation, an incision is first made through the body wall into a body cavity typically using a trocar, an elongated tube having a three point sharpened distal end. The trocar is often supported in a cannula, a shorter tube which passes into the incision made by the trocar and lines the wall of the incision, providing a port for entry into the incision. Various laparoscopic instruments such as oculars, cameras, or instruments similar to scissors or pliers may be introduced into the incision through the cannula to perform the necessary operation. The cannula also typically includes a port for receiving gas which may be introduced into the body cavity through the incision to inflate the cavity to increase the accessibility of the surgical site.

In typical laparoscopic procedures with most existing laparoscopic instruments, in order to close the incision and suture any cuts made in the cavity, it is necessary to remove the cannula, deflating the surgical cavity, and introduce a new suture guide which may have ports for needles connected to sutures for closing the incision. Other newer suturing devices do not require the removal of the cannula in order to introduce suturing devices, in that the suturing device itself is inserted through the center of the initial cannula. These suturing devices are cost prohibitive. Accordingly, after the suture carrying cannula or the suturing device is introduced, it is typically necessary to reinsufflate the body cavity.

SUMMARY OF THE INVENTION

The present invention is directed toward a single laparoscopic tool which allows a surgeon to make an incision; enter a body cavity; inflate the cavity; perform an operation through the cannula of the tool, which serves as a port, along with other instruments inserted through additional ports; and then close the incision through the same cannula with a suture carried by one or more needles passed through passages formed through the wall of the cannula. Therefore, the entire operation from incision to suturing can be performed with a single cannula, substantially simplifying the operative process relative to previous laparoscopic techniques.

In a preferred embodiment of the invention, which will be subsequently described in detail, a generally cylindrical cannula has a laterally enlarged section at its proximal end, which end lies externally of an incision, containing one or a pair of inclined passages for receiving suture needles passing through the side walls of the cannula, where they allow the needles to enter the interior volume of the tubular section of the cannula. In the two needle version, needles inserted into these inclined passages from the proximal end cross one another, with slight lateral separation, approximately midway through the length of the tubular section of the cannula. Another pair of passages in the opposed side walls of the tubular section of the cannula are formed near the distal end and align with the two passages at the proximal end so that a suturing needle passed into the top of the cannula through one of the inclined passages extends across the width of the tubular section and can exit the cannula at one of the two distal passages.

Shortly beyond the proximal end of the cannula, each of the inclined passages passes through manually actuable valves which may be opened to allow the needles to pass through them and may be closed when the needles are removed to prevent the escape of the insufflating gases which have been passed through the cannula and into the body cavity.

A gas conduit controlled by a valve preferably feeds into one of the inclined passages at the proximal end of the cannula, when there is no needle in that passage, to allow inflation of the body cavity to provide clearance for the surgical operation. The proximal end of the tubular passage through the cannula carries a flap valve near its upper end which closes under the pressure of insufflating gases to prevent the escape of the gases through the proximal end of the cannula port.

The suturing needles used with the present invention must pass through a portion of the body wall section when they exit through the distal passages through the cannula wall so that the sutures can engage and bring together portions of the body cavity on opposed sides of the cannula in order to close off the incision. Accordingly, the suture needles must have the ability to cut through the cavity wall. The suture needles are accordingly formed with a central cylindrical section which has a blunt distal end with a suture-engaging configuration. The proximal end of the suture needle is disposed within a handle where it is engaged by a compression spring which biases the cylindrical section toward an extended position from the handle. The cylindrical section is surrounded by a sheath which has a pointed distal end capable of cutting through tissue. The proximal end of the cutting sheath is fixed to the handle. When the blunt end of the tubular section is unobstructed, the spring bias causes it to extend beyond the end of the cutting sheath. When the needle is pressed against the body wall, the blunt end of the tubular section is forced against the spring bias and the pointed end of the cutting sheath extends downwardly into the tissue so that upon further pressure on the handle of the needle it cuts through the tissue, outside of the wall of the body cavity, so that a suture carried by the distal end of the needle is within the body cavity. The free end of the suture within the body cavity is then grasped by a pliers-like tool introduced into the body cavity from another port and manipulated by the surgeon using an endoscope, introduced through still another port, to view the interior of the body cavity.

A second suturing needle is then introduced through the other cavity in the cannula so that it pierces the tissue of the body cavity at a point displaced from the point of entrance into the cavity of the first suturing needle. The pliers-like tool may be used to join the free end of the suture to the distal end of the second needle. The second needle is then pulled back through the cannula to the exterior of the body cavity where the two ends of the suture may be knotted to secure the incision.

In one alternative embodiment of the invention, the cannula has only a single inclined passage for a suture needle which is used to carry a suture into the body cavity. The free end of the suture within the body cavity may then be grasped by an instrument introduced through a second port and detached from the needle. The entire cannula may then be rotated about its central axis while in the incision so that the suture may be reinserted on the needle end and drawn through the cannula passage, allowing the two ends of the suture to be knotted to close the incision. The two passage embodiment avoids the need to rotate the cannula within the cavity which may induce bleeding from the incision.

The insufflating gas used in laparoscopic operations is typically $CO_2$ because it is so easily absorbed in the body tissues and leaves no residue. The $CO_2$ may be combined with other similarly absorbable gases. Because of the high absorbability of the $CO_2$ in body tissues, a constant supply of the gas must be fed into the body cavity during the operation to maintain insufflation of the body cavity. In situations in which the distal exit cavities of the suturing needles from the cannula are located within the abdominal wall, rather than within the cavity itself, there is a possibility of $CO_2$ in liquids seeping into the tissue under pressure, causing subcutaneous emphysemas or other undesirable side effects.

In another alternative embodiment of the invention, in order to prevent the seepage of the gases into the tissues, a tubular sleeve is supported on the outer diameter of the cannula in such a way that it may be moved, typically manually, between a first position in which it covers the exit ports of the needle passages in the cannula to prevent the inflating gases from being introduced into the body tissue, and a second position, closer to the proximal end of the cannula, in which the sleeve does not extend over the outlet ports and allows the suturing needles to be introduced. Longitudinally extending tongues projecting from the opposed inner surfaces of the sleeve ride in longitudinal grooves formed in opposed sides of the cannula to guide the sleeve.

BRIEF DESCRIPTION OF THE DRAWINGS

Other objects, advantages, and applications of the present invention will be made apparent by the following detailed description of preferred embodiments of the invention. The description makes reference to the accompanying drawings in which:

FIGS. 1-5 all represent sections through the wall of a body cavity in which the first embodiment of the cannula of the present invention has been inserted and the sequential steps employed in performing suturing of the wall of the body cavity using the cannula and the suturing needles of the present invention;

DETAILED DESCRIPTION OF PREFERRED EMBODIMENTS OF THE INVENTION

Figures 6, 7:
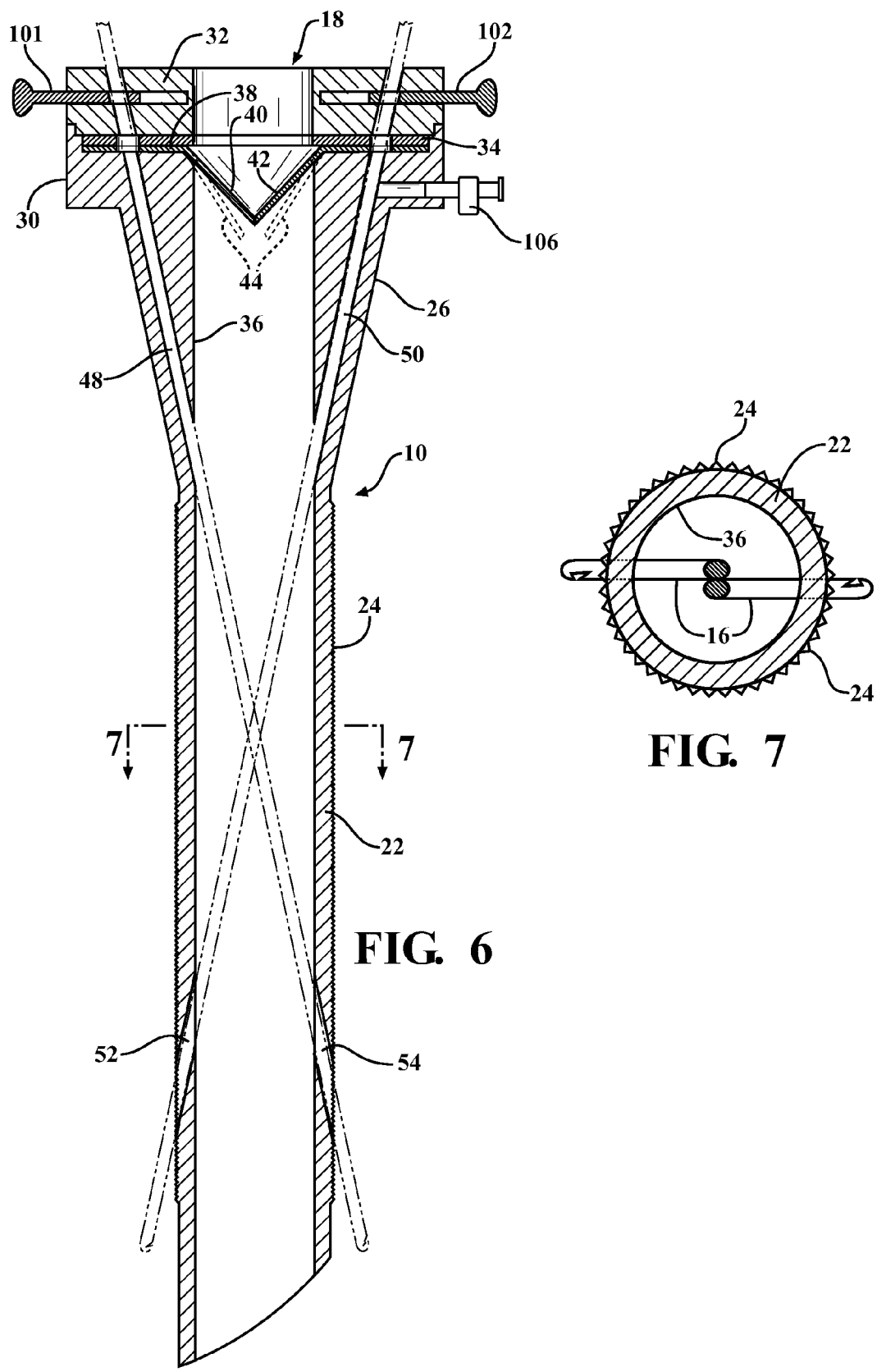
FIG. 6 is a cross-sectional view of the cannula of the present invention illustrating the paths of the two suturing needles in phantom lines.
FIG. 7 is a cross section through the drawing of FIG. 6, taken along line 7-7, illustrating the relationship of the two suturing needles as they pass through the barrel of the cannula.

FIGS. 1-5 illustrate a first embodiment of a cannula, generally indicated at 10, disposed in an operating position within a wall, generally indicated at 12, of a body cavity 14. These drawings illustrate the sequence of operations in utilizing the cannula 10 and a pair of suture needles 16 to close the incision in the body wall 12 required to position the cannula 10 with its proximal end 18 externally of the body cavity and its distal end 20 within the body cavity.

The cannula 10, illustrated in cross section in FIGS. 6 and 7, includes a tubular section 22 of somewhat greater length than the body wall 12 so it may extend through the body wall with its lower end 20 in the underlying body cavity 14. The tubular section 22 is formed with serrations 24 on its surface to firmly secure it within the body wall 12.

At the proximal end of the cannula 10 the side walls of the cannula flare outwardly in a section 26 so that the width of the cannula on the proximal side of the tubular section 24 has a greater width than the balance of the tubular section.

At the extreme proximal end of the cannula 10 the walls extend laterally in a section 30 and a top member 32 is connected to the proximal end of the section 30 with a gasket 34 between them. The gasket 34 has a central hole which allows the continuation of the interior wall 36 of the tubular section 22 to extend the full length of the trocar 20, as is best seen in FIG. 6. A second gasket 38 is disposed directly beneath the gasket 34. The gasket 38 has a pair of wall sections 40 and 42 at its center which act as a flap valve. In FIG. 6 the flap valve sections 40 and 42 illustrated in full line are shown closed and in dotted lines 44 are shown in an open position. The flap sections 44 are normally in the open position but when gas pressure is experienced on their distal side they are forced into the closed position of the full lines 40, 42.

As shown in FIG. 6, a pair of inclined suture cavities 48 and 50 are formed through the sections 26, 30 and 32. Their proximal ends open at the top of the section 32 and the lower ends of these passages 48 and 50 merge with the tubular interior 36 of the trocar at the distal end of the wall section 26. The passages 48 and 50 are adapted to receive two suture needles 16 which pass through the trocar 10 in the manner illustrated in the dotted lines in FIGS. 2, 4 and 6. The distal ends of the suture needles 16 pass through the side walls of the tubular section 22 of the trocar at a pair of slots in the side wall 52 and 54.

As is best seen in FIG. 7, the proximal passages 48 and 50 for the suture needles and the distal passages 52 and 54 are slightly separated laterally so that the two needles do not interfere with one another at the cross section 7-7 of FIG. 6.

Figure 8:
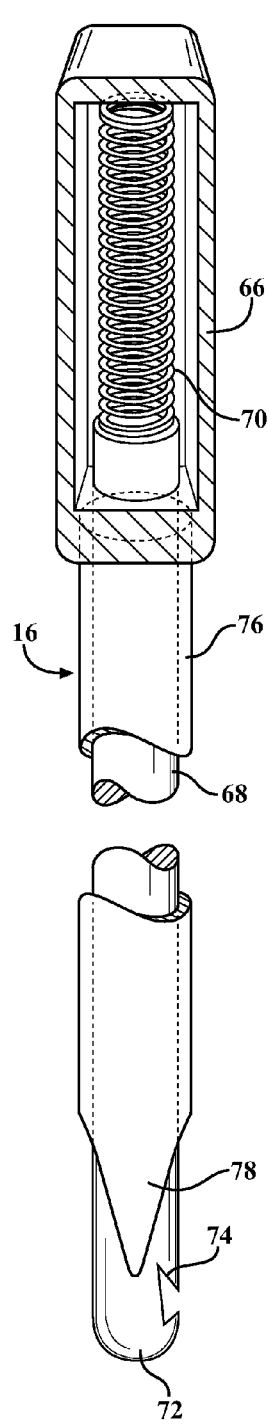
FIG. 8 is a sectional view, partially broken away, of the suturing needle of the present invention.

The needles 16 are illustrated in detail in FIG. 8. The two suture needles are substantially identical. They each have a handle 66 at the proximal end and a cylindrical straight needle 68 having its proximal end within the handle 66 bearing against a compression spring 70. The compression spring biases the needle cylinder 68 toward an extended position from the handle. The lower end of the needle 68 has a blunt end 72 and a side slot 74 adapted to capture a suture. The outer side of the tubular inner member 68 is surrounded by a tubular sheath 76 which has its proximal end fixed with respect to the handle 66 in such a manner that it is not subjected to the biasing action of the spring 70. The distal end of the sheath 76 terminates in a sharpened cutting edge 78.

When the suture needle 16 is manually pressed downwardly against a resistive surface such as the tissue of the body cavity 12, the blunt end 72 forces the tube 68 to move upwardly within the handle compressing the spring 70 until the cutting tip 78 of the outer sheath 76 extends beyond the end 72 of the tube 68 and begins to penetrate the body tissue. When the cutting edge 78 has passed through the wall 12 into the body cavity 14, there is no longer any pressure on the end 72 and it extends beyond the cutting tip 78 under the spring bias, so that the cutting tip 78 will not contact the interior body organs.

Figure 9:
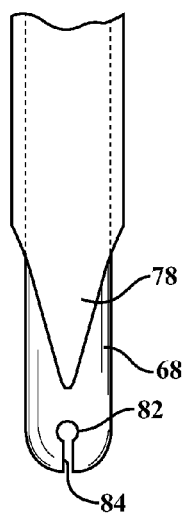
FIG. 9 illustrates the cutting end of an alternative form of suturing needle.

FIG. 9 illustrates an alternative form for the end of the tube 68. Rather than having the edge configuration 74, a hole 82 connected to the bottom of the needle 68 by passage 84 is employed. The suture may be forced through the narrow neck of the passage 84 into the hole 82 to retain the suture.

Figure 10:
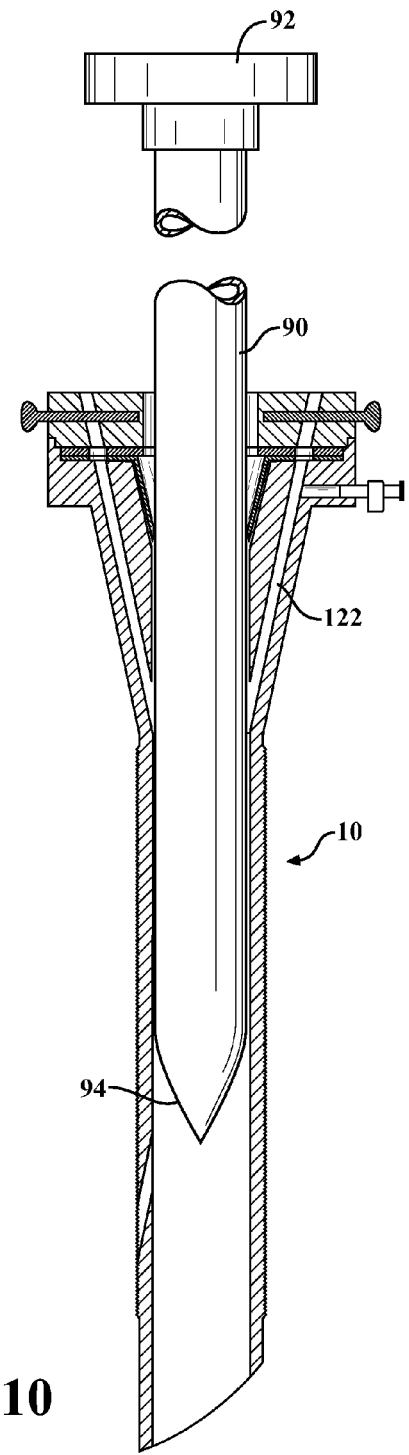
FIG. 10 is a cross-sectional view of the first embodiment of the cannula of the present invention with a trocar inserted into the barrel of the cannula.

FIG. 10 illustrates a preferred manner of performing an incision through the body wall 12 so that the cannula 10 may line the incision and act as a port for the insertion of various laparoscopic instruments such as endoscopes, surgical cutters, and the like.

Figure 11:
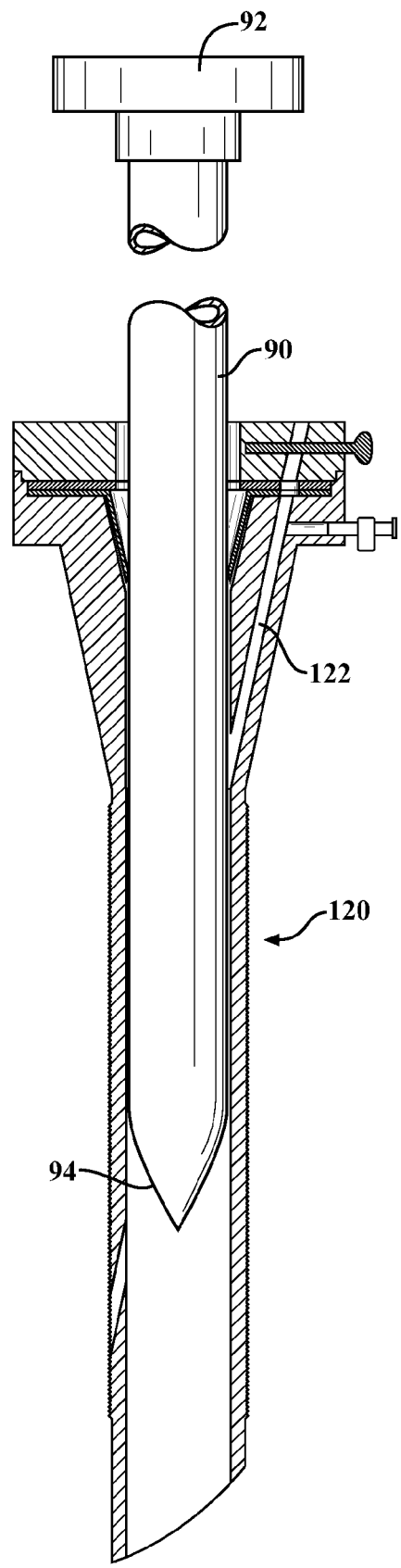
FIG. 11 is a cross-sectional view of a second embodiment of the cannula of the present invention with a trocar inserted into the barrel of the cannula.

The cannula generally indicated at 120 in FIG. 11 represents an alternative embodiment having only a single inclined passage 122 for a suture needle. Otherwise, it is the same as the two passage embodiment and is similarly numbered. Accordingly, after a suture has been introduced to the body cavity 14 through the single passage, it must be grasped by an instrument 112 introduced through a second port and freed from the needle. The cannula 20 is rotated by 90 degrees about its central axis within the incision. The instrument 112 then reattaches the suture to the needle and the needle and attached suture are withdrawn through the trocar and the two ends of the suture are knotted to close the incision.

To start the incision a surgeon will use a scalpel to make a small cut through the outer edge of the body wall 12 and then will bring the slanted end 20 of the cannula 10 or 110 into contact with the incision. A trocar 90 (FIG. 10) is then inserted through the central passage 36 of the cannula 110. The trocar has a handle 92 at its proximal end and a sharpened cutter 94 at its distal end. By pressure imposed on the handle 92, the trocar 94 will be forced through the body wall to form the laparoscopic incision. When the trocar end 94 is passed into the body cavity 14, the cannula 10 is pressed down through the incision and the trocar is withdrawn.

The proximal ends of the two suture needle passages 48 and 50 in the cannula 10 are controlled by two valves 101 and 102. These valves may be pushbutton valves or rotatable valves and they may be moved between a position in which the passages 48 and 50 are closed and positions wherein they are open to allow the entry of suture needles 16. After the incision is made, with the valves 101 and 102 closed off, valve 106 which is connected to a source of inflating gas, preferably $CO_2$, is opened to feed $CO_2$ gas into the passage 50 leading to the interior volume 36 of the cannula 10 and into the body cavity 14. The $CO_2$ inflates the body cavity to enlarge its area and provide the surgeon with increased operating room. After the cavity 14 is filled and inflated, the valve 106 is closed off.

The cannula 10 is then ready for use as a port for the performance of a laparoscopic operation and various devices such as an endoscope, a surgical cutter, and the like may be passed through the port.

The surgeon will typically create one or more additional ports at spaced points on the outer surface of the body tissue so that various operations may be performed through certain of the ports under a physician's observation through an endoscope in an additional port.

After the laparoscopic operation is completed, it is necessary to suture the incisions used to form the ports. This is generally done in the sequence illustrated by FIGS. 1-5 using the two needle trocar. First, a suture 100 is connected to the distal end of a suture needle 16, one of the valves 101 or 102 is opened, and the needle is passed through that valve and through the interior of the cannula and out one of the exit ports 52 or 54, cutting passages through the body tissue on the distal side of the passages 52 or 54. This brings one end of the suture 110 into the body cavity 14 as illustrated in FIG. 2.

Next, as illustrated in FIG. 3, the free end of the suture is grasped by an instrument 112 which is introduced through another port (not shown) into the incision. The instrument 112 removes the suture from the end of the needle and the needle may then be withdrawn from the cannula and its entry valve closed, or it may be left within the cannula. Then, as illustrated in FIG. 4, a second needle, or the same one that inserted the suture into the body cavity, if it has been removed, is inserted into the cavity through the opposite inclined passage used for the first insertion. The instrument 112 is manipulated to engage the free end of the suture with the suture engaging formation either 74 or 82 at the end of this needle within the incision and, as shown in FIG. 5, the free end of the incision is pulled back through the passage occupied by the suture needle so that both free ends of the suture extend out of the proximal section 18 of the cannula. The cannula may then be removed and the suture knotted to close up the incision.

The cannula 10 may be removed from the incision at any time after the operation is completed. During the execution of the operation there is no need to lose the insufflating gas pressure so that the incision needs to be reinflated and the cannula 10 acts as a port for use in the entire operation.

Figure 12:
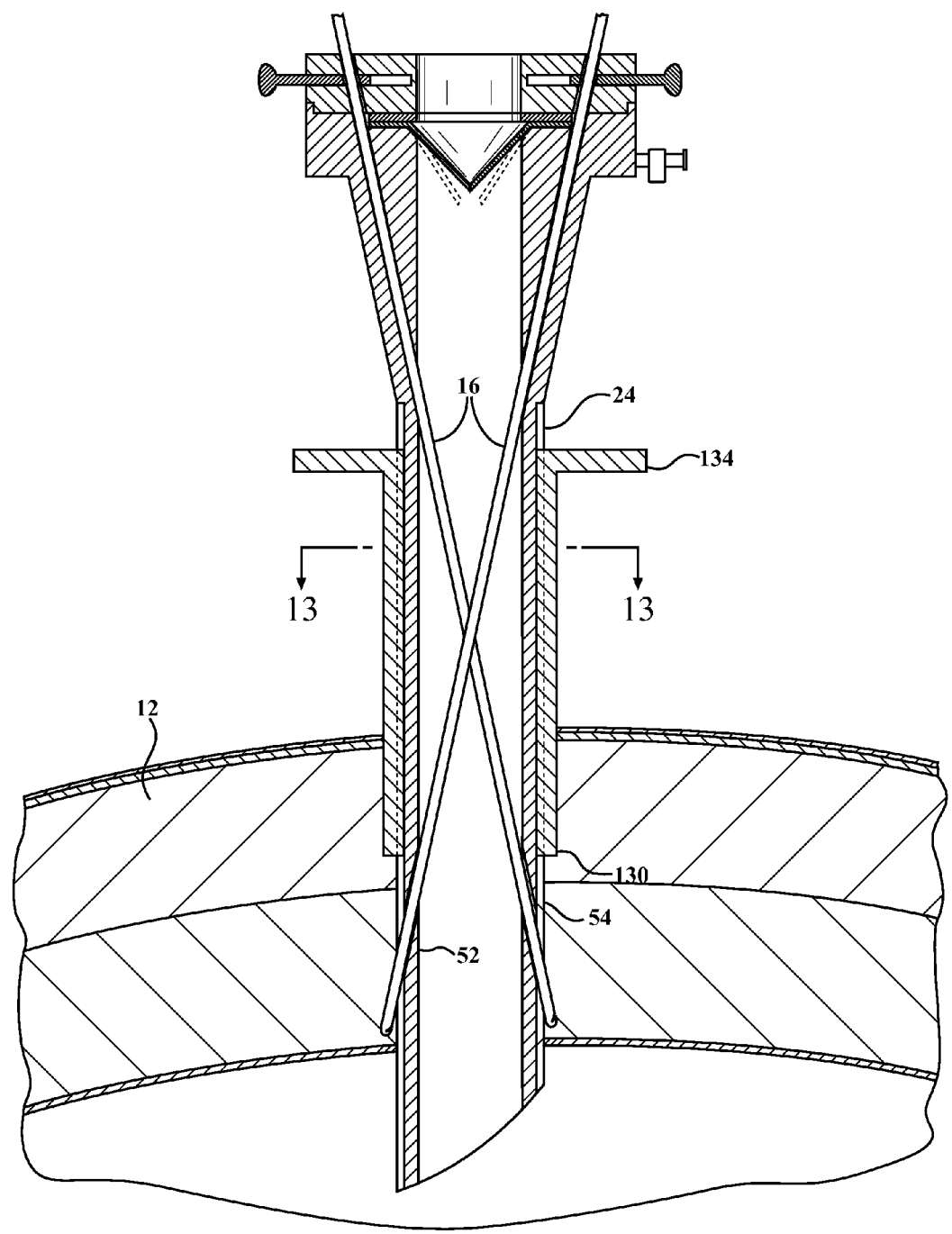
FIG. 12 is a sectional view of an alternative form of my invention with a sliding sleeve to close the outputs of the needle passages when they are not accommodating needles.
Figure 13:
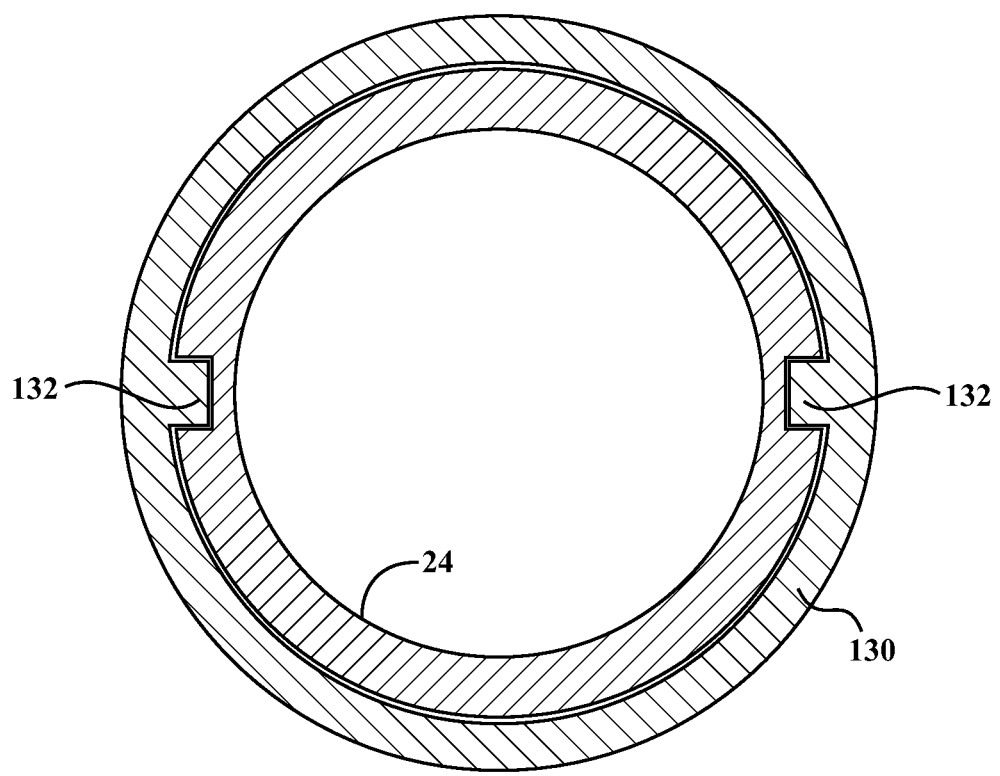
FIG. 13 is a section through the cannula and sleeve along section 1A of FIG. 12.

Another embodiment of the invention is illustrated in FIG. 12 which is directed toward avoiding the danger of the insufflating gas, which maintains the gas pressure in the body cavity during the procedure despite losses of the gas by being absorbed in the body tissue flowing out the ports 52 and 54 into the tissue of the cavity wall 12. This could cause subcutaneous emphysema or other undesirable effects. This is not a problem if the ports are within the body cavity 14, but is a danger if the needle outlet ports fall within the thickness of the body wall over the cavity.

Figure 14:
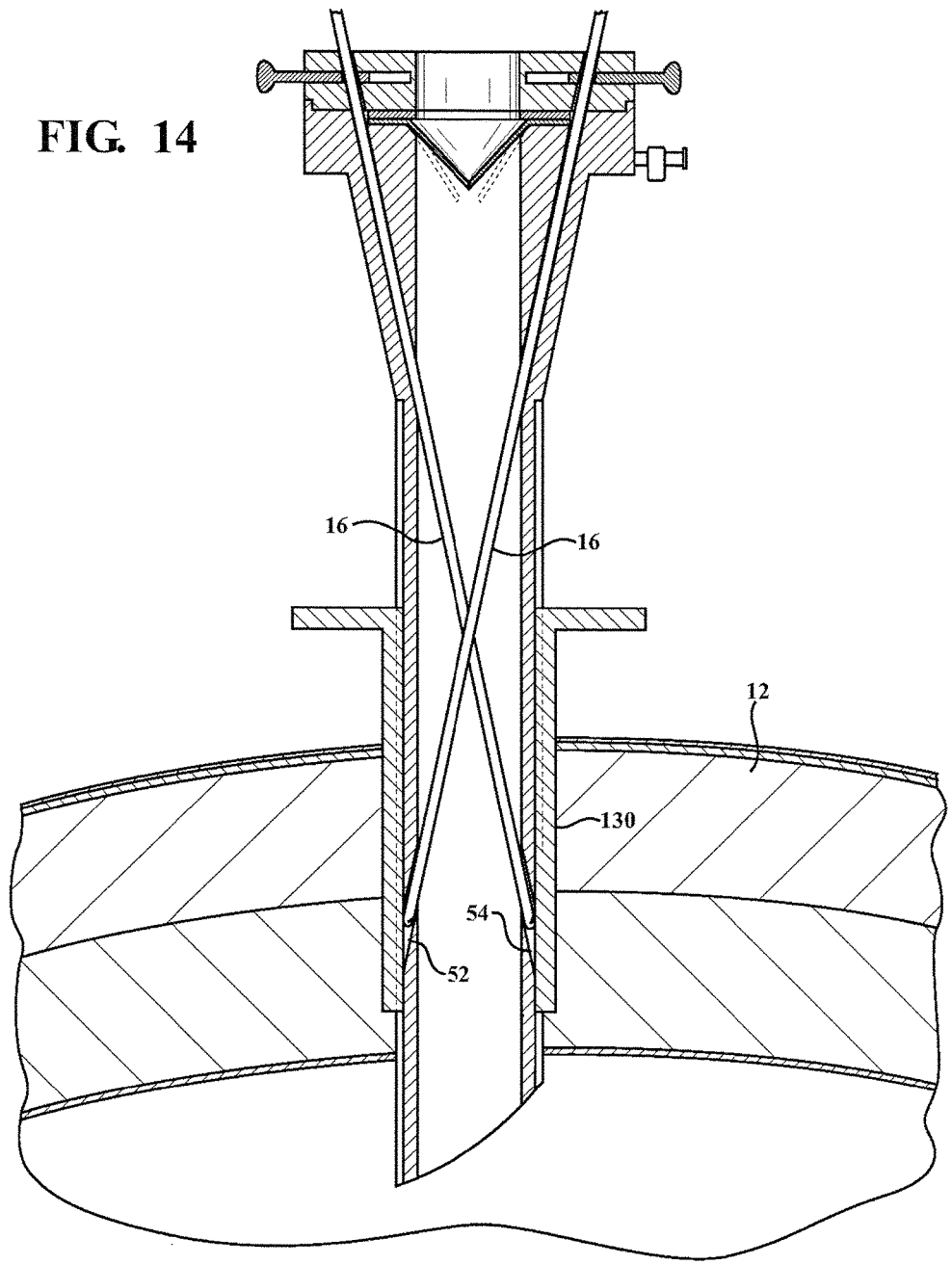
FIG. 14 is a view similar to FIG. 12 showing the sleeve blocking the exit ports of the needle passages.

Accordingly, a tubular sleeve 130 of a thin but rigid material, such as stainless steel or plastic, surrounds the lower section of the cannula wall 24. As disclosed in the cross section 13-13 through the sleeve 130 and the wall 24, in this embodiment the lower, tubular section of the cannula wall 24 is formed with a pair of longitudinal slots on diametrically opposed points. The tubular sleeve 130 is formed with complementary tongue members 132 that extend into the slots. Through a radially outward handle member 134 formed at the top of the sleeve 130, the sleeve may be manually moved by the surgeon between an upper position illustrated in FIG. 12, wherein its lower end is above the outlet ports 52 and 54 allowing the lower ends of the needles 16 to project out of the ports and a lowered position, illustrated in FIG. 14, in which the lower ends of the tube 130 block the exit ports so that the insufflation gases cannot penetrate the cavity wall 12. When the needles 16 project through the outlet ports 52 and 54, as illustrated in FIG. 12, they block the flow of insufflation gases through the ports. In a further embodiment, the blocking member is formed of a sheet of metal or plastic.

Having thus disclosed my invention I claim:

1. A cannula for use in laparoscopic surgery performed through a wall of a body cavity, the cannula comprising:
   an elongated tubular section having a tubular section proximal end, a tubular section distal end, and a wall, the wall having an interior surface defining an interior of the tubular section and an exterior surface, the tubular section open at both the proximal and distal ends and having a central axis;
   a first passage through the wall of the tubular section, inclined with respect to the central axis, the first passage comprising a first opening through the wall of the tubular section at a position adjacent the proximal end of the tubular section, and a second opening through the wall of the tubular section adjacent to the distal end of the tubular section at a position on the tubular wall diametrically opposed to the position of the first opening, the first and second openings being aligned so that a first straight suture needle may be passed through both the first and second openings with a section of the needle intermediate the first and second openings transversing an interior of the tubular section at an angle of inclination to said central axis, and with a distal end of the needle projecting out of the second opening and through the wall of the body cavity; and
   a blocking member having a blocking member proximal end and a blocking member distal end, the blocking member slidably supported on the elongated tubular section for motion along said exterior surface of the wall of the tubular section between a first position in which the blocking member blocks flow of gases through said second opening and a second position clear of said second opening allowing passage of said first straight suture needle through said second opening, wherein the blocking member distal end is spaced apart from the distal end of the tubular section and is located proximal to the second opening when the blocking member is in said second position.

2. The cannula of claim 1, wherein said blocking member comprises a tubular sleeve surrounding the tubular section of the cannula.

3. The cannula of claim 2, where the blocking member is formed of a sheet of metal.

4. The cannula of claim 2, where the blocking member is formed of sheet plastic.

5. The cannula of claim 1, wherein the blocking member carries a projection extending radially outward relative to the central axis of the tubular section for use in movement of the blocking member between its first and second positions.

6. The cannula of claim 1, wherein a pair of grooves extend parallel to said central axis on diametrically opposed sections of the exterior surface of the tubular section and the blocking member comprises a pair of inward radially extending tongue members adapted to ride in said grooves.

7. The cannula of claim 1, further including a second passage through the wall of the tubular section at a position diametrically opposed to the first passage, the second passage being inclined with respect to the central axis of the tubular section at an angle complementary to the angle of inclination of the first passage, so that extensions of the first and second passages cross one another at a position in a central region of the tubular section; whereby said first straight needle may be passed through the first passage and a second straight needle may be passed through the second passage, exiting the tubular section through a third opening radially opposite to said second opening and said blocking member, when in its first position, blocks the flow of gases through both said second opening and said third opening.

* * * * *